United States Patent [19]

Mendiratta

[11] Patent Number: 4,529,823
[45] Date of Patent: Jul. 16, 1985

[54] PURIFICATION OF BISPHENOL-A

[75] Inventor: Ashok K. Mendiratta, Schenectady, N.Y.

[73] Assignee: General Electric Company, Schenectady, N.Y.

[21] Appl. No.: 596,138

[22] Filed: Apr. 2, 1984

[51] Int. Cl.³ .............................................. C07C 37/84
[52] U.S. Cl. ................................... 568/724; 568/748; 568/749
[58] Field of Search ......................... 568/724, 748, 749

[56] References Cited

U.S. PATENT DOCUMENTS

| | | | |
|---|---|---|---|
| 2,791,616 | 5/1957 | Luten, Jr. | 568/724 |
| 3,192,270 | 6/1965 | Meyer et al. | 568/724 |
| 3,326,986 | 6/1967 | Dugan et al. | 568/724 |
| 4,192,955 | 3/1980 | Reinitz | 568/724 |
| 4,209,646 | 6/1980 | Gac et al. | 568/724 |
| 4,467,119 | 8/1984 | Thomas | 568/724 |

FOREIGN PATENT DOCUMENTS

| | | | |
|---|---|---|---|
| 2548470 | 5/1976 | Fed. Rep. of Germany | 568/724 |
| 1528935 | 6/1968 | France | 568/724 |
| 159733 | 10/1982 | Japan | 568/724 |
| WO80/00150 | 2/1980 | PCT Int'l Appl. | 568/724 |

*Primary Examiner*—Werren B. Lone
*Attorney, Agent, or Firm*—Richard J. Traverso; James C. Davis, Jr.; James Magee, Jr.

[57] ABSTRACT

This invention is directed to a method of purifying crude bisphenol-A by crystallization with agitation in phenolic water having less than 30 weight percent phenol. The crystals obtained have a morphology similar to that of aqueous crystallized bisphenol-A with a significantly higher degree of purity than crystals obtained from an aqueous crystallization. The use of an organic solvent, foreign to the bisphenol-A synthesis reaction, for either washing or crystallization can be avoided and only small quantities of phenol and water are required when providing pure bisphenol-A for polycarbonate synthesis by this process.

12 Claims, No Drawings

PURIFICATION OF BISPHENOL-A

CROSS REFERENCE TO RELATED APPLICATION

Reference is made to copending application Ser. No. 443,344 filed Nov. 15, 1982, assigned to the same assignee as the present invention.

BACKGROUND OF THE INVENTION

This invention is concerned with the purification of bisphenol-A (or BPA), the most common species being 2,2-bis(4-hydroxyphenyl)propane. More particularly, this invention is directed to a method of recovering bisphenol-A in a purified state from crude bisphenol-A by crystallization in phenolic water of a particular phenol/water ratio.

Crude bisphenol-A is the isolated product of commercial processes for preparing bisphenol-A. It is a mixture of bisphenol-A and impurities derived from a BPA synthesis reaction. An example of a BPA synthesis reaction is the acid-catalyzed condensation of phenol and acetone, where phenol and acetone react in the presence of an acidic material, such as sulfuric acid, hydrochloric acid, cation exchange resin, etc.

The crude bisphenol-A produced contains undesirable impurities such as phenol, 2-(4-hydroxyphenyl)-2-(2-hydroxyphenyl)propane having the formula

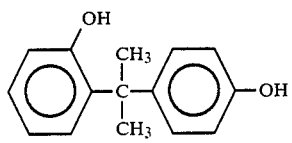

a trishydroxyphenyl compound of the formula

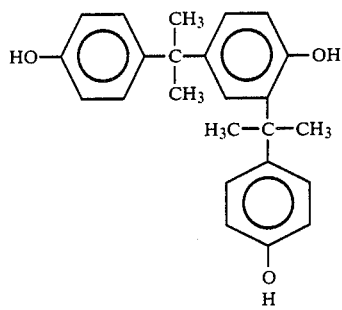

and small amounts of other impurities such as the two compounds having formulas

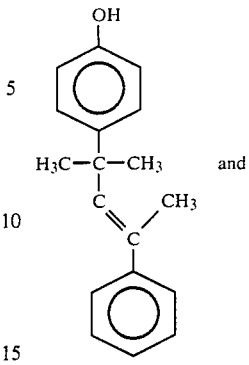

and

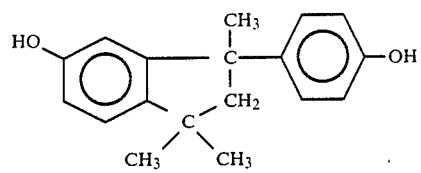

and some impurities which discolor the crude bisphenol-A with unknown structure (herein identified as color bodies).

Since bisphenol-A is used in making polycarbonate resins by reaction of the former with either phosgene or diphenyl carbonate, or for making epoxy resins, both resins being used extensively in commercial applications involving molding, casting and sheet forming processes, it is highly important that the monomeric bisphenol-A used to make such resins be as pure as possible in order to avoid adverse effects on the properties of the polymers thus obtained.

The preparation of bisphenol-A by the acid catalyzed reaction of phenol and acetone is usually carried out in excess phenol (2 or more moles per mole of acetone). This reaction mixture is typically subjected to a series of distillation steps to remove the excess phenol, acetone and water or the acetone and water are removed and the bisphenol-A/phenol adduct is crystallized from excess phenol, followed by stripping of the phenol. Both procedures provide liquid crude bisphenol-A which is the starting point for making bisphenol-A of high purity. Distillation or stripping of the phenol from the reaction mixture can be carried out only to a limited extent on account of the thermal instability of the bisphenol-A product.

A conventional method of recovering pure bisphenol-A product from crude bisphenol-A involves crystallization in the presence of an organic solvent. The crude molten bisphenol-A is first dissolved in a suitable organic solvent and the solution is then cooled to yield pure bisphenol-A crystals, which are recovered by filtration. However, this process suffers in that (1) the crystals produced are fine, powdery and needle-like and are difficult to handle, store and dry; (2) these crystals permit some organic solvent to occlude during crystallization, which cannot be removed during the drying step and hence is present in the polymerization process and (3) these processes require the use of a foreign organic solvent. The expression "foreign organic solvent" being defined herein as any organic solvent which is not utilized in the synthesis of bisphenol-A. These are typically organic solvents other than phenol and acetone. The use of foreign organic solvents is undesirable since they must be dealt with separately when isolating pure bisphenol-A.

A method which uses water as a crystallization medium for crude bisphenol-A is described in U.S. Pat. No. 3,326,986. According to this patent, the isolated crude bisphenol-A in molten form is purified by first mixing with water and cooling the mixture to yield large, rhombic crystals of bisphenol-A. The crystallization in water does not provide purification; however, separation of these crystals from the mother liquor, followed by an organic solvent wash, results in purified bisphenol-A. Although the process described within the above-referenced patent avoids occlusion by an organic solvent during the crystal formation step and yields large, less needle-like crystals that are easy to handle, quantities of a foreign organic solvent are utilized to wash the crystals.

It is desirable to obtain a high degree of purification without the use of a foreign organic solvent and maintain the large, rhombic character of the aqueous crystallized bisphenol-A.

The process described in copending allowed application Ser. No. 443,344, describes a washing procedure for purifying aqueous crystallized bisphenol-A with a water/organic solvent wash, the organic solvent being water immiscible. Although the process provides large, purified crystals of bisphenol-A which are easy to handle, the use of a "foreign organic solvent" is required. The process comprising this invention obtains large, highly purified bisphenol-A crystals by utilizing phenolic water (phenol being a non-foreign organic solvent) of a particular phenol/water ratio as a crystallization solvent. Although Luten describes the "breaking" of a bisphenol-A phenol adduct with water in U.S. Pat. No. 2,791,616, large amounts of phenol and water are used with little or no purification, as shown in Example VIII below and the BPA crystals obtained are fine and needle-like. Reinitz describes the use of a phenol/water mixture with a foreign organic solvent as a crystallization medium for bisphenol-A in U.S. Pat. No. 4,192,955. This process does not provide bisphenol-A having a crystal morphology which matches that provided by an aqueous crystallization. Comparing Examples VIII and IX to the Examples which illustrate the process comprising this invention demonstrates the substantial improvement in bisphenol-A crystal morphology and purity over the purification processes described in these references which utilize phenol and water both with and without a foreign organic solvent. In addition, the process comprising this invention obtains high yields of purified bisphenol utilizing small quantities of water and phenol and no foreign organic solvents.

SUMMARY OF THE INVENTION

A method of purifying crude bisphenol-A is provided comprising crystallizing crude bisphenol-A with agitation in less than 3 parts by weight phenolic water having less than 30 wt.% phenol, separating the bisphenol-A crystals from the phenolic water, contacting said bisphenol-A crystals with an aqeuous washing solvent and recovering the bisphenol-A crystals. The quantity of aqueous washing solvent is preferably less than 3 parts by weight per part of the bisphenol-A crystals. This aqueous washing solvent can contain a quantity of about 0 to 20 wt. % phenol to provide further purification when necessary.

OBJECTS OF THE INVENTION

An object of the present invention is to purify crude bisphenol-A without utilizing a foreign organic solvent.

Another object of the present invention is to provide bisphenol-A crystals of high purity of a rhombic shape and large size.

Another object of the present invention is to provide a simple method for purifying crude bisphenol-A which comprises a relatively small number of steps and procedures.

Another object of the present invention is to provide a process for purifying crude bisphenol-A utilizing small quantities of water and phenol.

Another object of the present invention is to provide a method for purifying crude bisphenol-A which provides high yields of purified bisphenol-A crystals.

Other objects of this invention shall become apparent in the detailed description of the preferred embodiments.

DETAILED DESCRIPTION OF THE PREFERRED EMBODIMENTS

The objects of the present invention, and other objects, are achieved by crystallizing crude bisphenol-A in phenolic water, having less than 30 wt. % phenol with agitation.

The crude bisphenol-A produced from a BPA synthesis reaction is typically in the form of a liquid residue as when crude bisphenol-A is produced from the acid-catalyzed condensation reaction with phenol and acetone where the excess phenol, acetone and water are removed from the reaction medium. To achieve the desired objects of this invention, it is not necessary to remove all the excess phenol and water from the reaction mixture containing crude bisphenol-A provided that the ratios of phenol/water do not exceed the limits described below. The crude bisphenol-A purified by this process need not be a liquid residue and need not be the product of an acid-catalyzed reaction. Solid crude bisphenol-A can be purified by this process by heating the bisphenol-A/phenolic water mixture to a temperature of about 92° to 100° C. to melt the solid bisphenol-A prior to purification by crystallization.

Typically the crude bisphenol-A to be purified by this process is molten and crystallization can be effected by simply adding phenolic water in a quantity more particularly described below and cooling the mixture to a temperature in the range of about 60° to 70° C. and less. The quantity of phenolic water utilized as a crystallization medium is not critical to achieve the desired objects of this invention. However, it is preferable to utilize less than 3 parts by weight phenolic water per part of the crude bisphenol-A to be crystallized. The molten crude bisphenol-A and phenolic water exist in two phases, with the liquid crude bisphenol-A phase resting below the phenolic water phase. As the mixture cools with agitation, large crystals form and a slurry of BPA crystals and phenolic water is produced. Both water miscible and immiscible species dissolve in the phenolic water, leaving the bisphenol-A crystals substantially free of impurities and color bodies. The most preferred quantities of phenolic water utilized for crystallization of crude bisphenol-A fall within the range of about 1 to 1.5 parts by weight per part of crude bisphenol-A. Although larger quantities can be utilized, the purification obtained with such quantities does not increase significantly.

The expression "phenolic water" as used herein is intended to describe a solution substantially comprised of water and phenol. These solutions preferably comprise about 90 wt.% of a phenol/water mixture and most preferably about 99–100 wt.% of a phenol/water mixture. The phenolic water can contain other organic solvents, such as acetone, methylene chloride, substituted phenols, etc.; a base, such as alkali metal hydroxides, organic amines, alkali earth metal hydroxides, carbonates, etc. and other constituents subject to the proviso that (a) the constituent is soluble in the phenol/water mixture so as to provide a homogeneous solution and (b) the constituent does not cause the liquid crude bisphenol-A to become soluble in the phenolic water so as to cause crystallization to occur in a single homogeneous phase. As discussed above, it is undesirable to utilize foreign organic solvents in the purification process and it is most preferable to crystallize in phenolic water having about 100 wt.% of a phenol/water mixture.

The quantity of phenol present in the phenolic water can range between about 5 to 30 wt.% of said phenolic water. Quantities of phenol in excess of 30 wt.% cause the liquid crude bisphenol-A to become soluble in the phenolic water. As a result, crystallization occurs in a single homogeneous phase. This is undesirable since such a crystallization will not provide large, rhombic crystals of bisphenol-A. The degree of purification obtained is dependent on the quantity of phenol in the phenolic water. Large quantities of phenol maximize purification, but can cause smaller crystals to result and permit more phenol to remain with the product. The most preferred quantity of phenol in said phenolic water is between about 10 to 15 wt.%. Although purification is obtained when utilizing quantities of phenol less than 5 wt.%, the process may have to be repeated or other purification procedures may be necessary to provide an acceptable degree of purity.

The degree of purification and recovery of purified bisphenol-A obtained is dependent on the temperatures utilized during crystallization. The initial temperature should not exceed the reflux temperature of the phenolic water and the final temperature should not fall below the freezing temperature of said phenolic water. Final temperatures for crystallization typically fall within the range of from about 45° C. to 85° C. Both higher and lower temperatures are suitable however.

The source of the phenol for the phenolic water can be a portion of the excess phenol found in the reactor effluent of a BPA synthesis reaction. The reactor effluent typically contains a large excess of phenol and requires distillation of a portion of said excess phenol along with preceding members in the distillation train. Alternatively, all of the excess phenol within a BPA synthesis reactor effluent can be removed and fresh phenol can be utilized within the phenolic water or solid crude bisphenol-A can be melted and crystallized in the presence of fresh phenolic water.

Once the liquid crude bisphenol-A is crystallized in phenolic water, the bisphenol-A crystals are separated from the phenolic water by employing conventional solid/liquid separation equipment. The purified crystals are typically removed by a basket centrifuge or by filtration. The crystals will be water-wetted with a very low phenol content. As such, it is preferable to wash the crystals with an aqueous solvent to remove the residual phenol. Any quantity of aqueous washing solvent can be utilized; however, it is preferred to utilize 0.5 to 1.5 parts by weight of an aqeuous washing solvent per part of bisphenol-A crystals.

Where it is desirable to remove additional impurities from the bisphenol-A crystals, phenol may be utilized to wash the crystals or the aqueous washing solvent may contain a quantity of phenol, preferably within the range of from about 0 to 20 wt.% and most preferably about 10 to 15 wt.%. Alternative methods of removing additional impurities are the washing procedures described in copending application Ser. No. 568,017 and Ser. No. 443,344. These copending applications describe processes wherein bisphenol-A crystals are washed with an aqueous alkaline solution and an aqueous/water immiscible organic solvent solution, respectively. The wash with the aqueous washing solvent can be achieved in the equipment utilized to achieve separation of the bisphenol-A crystals and phenolic water. Examples of such equipment include a filter or centrifuge. Alternatively, the crystals can be washed by reslurrying in the aqeuous washing solvent and removal of said solvent by applying the same procedure described to separate the phenolic water.

Where the aqueous washing solvent contains a portion of phenol, it may be desirable to remove any phenol which resides on the washed bisphenol-A crystals. This can be accomplished by contacting the washed crystals with water, preferably in a quantity of about 0 to 1 part by weight water per part of bisphenol-A crystals. This second wash can be accomplished in the same manner as the preceding wash. After such a wash, the crystals are separated and dried to remove excess water. A slightly water wetted crystal may not be completely dried if used to form polycarbonate. Water is utilized in the polymerization process and its presence in the bisphenol-A starting material will not effect the finished product. Drying of purified bisphenol-A may be aided by the use of conventional equipment.

Bisphenolic compound other than the 2,2-bis-(4-hydroxyphenyl)propane described above, which can be purified in accordance with the process of this invention are, for example, bis(hydroxy-aryl)-alkenes such as 4,4'-dihydroxydiphenyl methane; 1,1-bis(4 hydroxyphenyl ethane, propane, butane, isobutane; 2,2-bis(4-hydroxyphenyl)butane and bis(4-hydroxyphenyl-ether), sulfide, sulfoxide and sulfone.

The impurities and small quantities of bisphenol-A which are solubilized by the phenolic water may be isolated and returned to the BPA synthesis reaction. After the bisphenol-A crystals are separated from the phenolic water, the impurities can be removed from the phenolic water by conventional methods. An example of such a method is a distillation procedure. Once the impurities are removed from the phenolic water, it may be recycled into this process or the phenol may be recovered and utilized in a BPA synthesis reaction.

The process comprising this invention has the advantage that only small quantities of phenol are necessary to purify the crude bisphenol-A and no foreign organic solvents need be utilized in this process. This process is also simpler in that all of the excess phenol in a BPA synthesis reactor effluent need not be removed. Another advantage to this process is that the crystals are large and rhombic in shape. These crystals are easy to handle in the equipment utilized to produce polycarbonate resin. In addition, these crystals are of high purity with fewer impurities being detected than in those produced by conventional processes. Such crystals are highly desirable in the production of polycarbonate resin.

The following examples are provided to further illustrate the invention. They are not provided to limit the invention to their contents.

EXPERIMENTAL

The following general crystallization/solid separation procedure was employed in Examples I-VI.

A 1000 ml flask equipped with an agitator, condenser and thermometer was immersed in an oil bath and charged with bisphenol-A, phenol and water in a ratio more particularly described in each example. The mixture was heated to 100° C., wherein two liquid phases were observed with no solids present. The mixture was cooled with agitation to effect crystallization of pure bisphenol-A. The solid crystals were separated at about 65° C. with the help of a basket centrifuge. The crystals were washed by pouring an aqueous washing solvent at 65° C. into the centrifuge. The crystals were then spun to near dryness and removed from the centrifuge.

The relative color content value was measured as the absorbance of a 10% solution (5 grams with 50 ml methanol) in a 10 cm cell at a wavelength of 350 nm. High pressure liquid chromatography was used for measuring the phenol level in the product bisphenol-A.

EXAMPLE I

The crystallizer feed comprised 255 grams bisphenol-A (initial absorbance value=0.32), 28 grams of phenol and 280 grams of water. After crystallization and separation of crystals, the solids obtained were washed with 280 grams of water at 85° C. The bisphenol-A recovered (225 grams, 88.2% yield) had an initial absorbance value of 0.17 with a phenol content of 0.3%.

EXAMPLE II

The crystallizer feed comprised 255 grams bisphenol-A (initial absorbance value=0.32), 28 grams phenol and 280 grams water. After crystallization and separation of crystals, the solids obtained were washed with 70 grams of phenol at 65° C. The bisphenol-A recovered (220 grams, 86.3% yield) had an initial absorbance value of 0.12 with a phenol content of 8.5%.

EXAMPLE III

The crystallizer feed comprised 255 grams bisphenol-A (initial absorbance value=0.32), 28 grams phenol and 280 grams water. After crystallization and separation of crystals, the solids obtained were washed with 70 grams of phenol at 65° C., followed by 1200 grams of a water wash at 85° C. The bisphenol-A recovered (201 grams, 78.8% yield) had an initial absorbance value of 0.10 with a phenol content of 1.5%.

EXAMPLE IV

The crystallizer feed comprised 255 grams bisphenol-A (initial absorbance value=0.32), 28 grams phenol and 280 grams water. After crystallization and separation of crystals, the solids were washed with 70 grams of phenol at 65° C. This was followed by reslurrying with 240 grams of water for ½ hour at 65° C. These solids were separated on a basket centrifuge at 65° C. and washed with 220 grams of water at 65° C. The bisphenol-A recovered (197 grams, 77.3% yield) had an initial absorbance value of 0.09 with a phenol content of 0.2%.

EXAMPLE V

The crystallizer feed comprised 255 grams bisphenol-A (initial absorbance value=0.32), 28 grams phenol and 280 grams water. After crystallization and separation of crystals, the solids were washed with 280 grams of phenolic water having 12% by weight phenol at 65° C. The bisphenol-A recovered (219 grams, 85.9% yield) had an initial absorbance value of 0.14 with a phenol content of 3.1%.

EXAMPLE VI

The crystallizer feed comprised 255 grams bisphenol-A (initial absorbance value=0.32), 28 grams phenol and 280 grams water. After crystallization and separation of crystals, the solids were analyzed to determine initial absorbance and phenol content without an aqueous solvent wash. The bisphenol-A recovered (226 grams, 88.6% yield) had an initial absorbance value of 0.17 with a phenolic content of 0.4%.

EXAMPLE VII

The crystallizer feed comprised 255 grams bisphenol-A (initial absorbance value=0.32), 28 grams phenol and 280 grams water. After crystallization and separation of crystals, the solids were reslurried with 240 grams of phenolic water (10% phenol in water) at 65° C. for ½ hour. After reslurrying, the solids were separated and washed with 240 grams of water at 65° C. The bisphenol-A recovered (203 grams, 79.6% yield) had an initial absorbance value of 0.09 with a phenol content of 0.2%.

EXAMPLE VIII

This example demonstrates the process disclosed by Luten, Jr. et al. To a 2000 ml flask equipped with an agitator, a condensor and thermometer were added 100 grams crude bisphenol-A/phenol adduct (30% phenol and 70% BPA Initial absorbance=0.32) and 1000 grams water. The mixture was stirred for ½ hour at 65° C. to "break" the adduct. The solid crystals were separated at 65° C. with the help of a basket centrifuge. The bisphenol-A provided (56.34 grams, 80.5% yield) had an initial absorbance value of 0.30 and a phenol content of 3%. The bisphenol-A crystals provided were washed twice with 100 gram portions of water at 65° C. on the centrifuge. The bisphenol-A crystals provided (55 gram, 78.6% yield) had an initial absorbance value of 0.30 and no detectable quantity of phenol.

EXAMPLE IX

This example demonstrates the process disclosed by Reinitz. To a 1000 ml flask equipped with agitator, condensor and thermometer were added 70 grams of crude bisphenol-A (initial absorbance value=0.32), 30 grams phenol and 200 grams methanol at room temperature. To this solution were added 800 grams of water at a temperature of 50° C. to produce a mixture. The resulting mixture was cooled to 25° C. to permit crystallization of bisphenol-A. The solids were separated at this temperature and analyzed. The bisphenol-A recovered (49.4 grams, 70.6% yield) had an initial absorbance value of 0.14 and no detectable phenol.

What is claimed is:
1. A method of purifying crude bisphenol-A comprising
   (a) forming an admixture of crude bisphenol-A and phenolic water having less than 3 parts by weight phenolic water per part of crude bisphenol-A, said phenolic water having about 5-30 weight percent phenol, said admixture having a temperature sufficiently high to melt said crude bisphenol-A;

(b) cooling said admixture to a temperature sufficiently low to crystallize bisphenol-A;

(c) separating the bisphenol-A crystals and phenolic water;

(d) contacting said bisphenol-A crystals with a washing solvent comprised of members selected from the group consisting of water, phenol and mixtures thereof; and (e) recovering said bisphenol-A crystals.

2. A method as in claim 1 wherein the washing solvent is an aqueous solution and less than 3 parts by weight of said aqueous solution per part of bisphenol-A crystals are utilized.

3. A method as in claim 1 wherein about 0.5 to 1.5 parts by weight of phenolic water per part of crude bisphenol-A are utilized to crystallize said crude bisphenol-A.

4. A method as in claim 1 wherein said phenolic water contains about 10 to 15 weight percent phenol.

5. A method as in claim 1 wherein said bisphenol-A crystals are contacted with a washing solvent comprised of about 0.5 to 1.5 parts by weight of an aqueous solution per part of bisphenol-A crystals.

6. A method as in claim 1 wherein said aqueous solution contains about 0 to 20 weight percent phenol.

7. A method as in claim 6 wherein said aqueous solution contains about 10 to 15 weight percent phenol.

8. A method as in claim 5 wherein said bisphenol-A crystals are contacted with an aqueous washing solvent containing about 10 weight percent phenol.

9. A method as in claim 1 wherein said crude bisphenol-A is crude 2,2-bis(4-hydroxy phenyl)propane.

10. A method as in claim 7 wherein the bisphenol-A crystals of step c are contacted with about 0 to 1 part by weight water per part of bisphenol-A crystals.

11. A method of purifying bisphenol-A comprising (a) forming an admixture of crude 2,2 bis(4-hydroxy phenyl)propane with about 1 part by weight phenolic water having about 10 weight percent phenol, said admixture having a temperature sufficiently high to melt said crude 2,2bis(4-hydroxy phenyl)propane;

(b) cooling said admixture to a temperature sufficiently low to crystallize 2,2 bis(4-hydroxy phenyl)propane;

(c) separating the 2,2 bis(4-hydroxy phenyl)propane crystals and phenolic water;

(d) contacting said 2,2 bis(4-hydroxy phenyl)propane crystals with about 1 part by weight of an aqueous washing solvent having about 10 weight percent phenol; and (e) recovering said 2,2 bis(4-hydroxy phenyl)propane.

12. A method as in claim 11 comprising the addition step of contacting the 2,2 bis(4-hydroxy phenyl)propane crystals of step c with about 0 to 1 part by weight water per part of said 2,2 bis(4-hydroxy phenyl)propane crystals.

* * * * *